US012673928B2

(12) United States Patent
Capuzzi et al.

(10) Patent No.: US 12,673,928 B2
(45) Date of Patent: Jul. 7, 2026

(54) PROCESS FOR THE PRODUCTION AND SEPARATION OF 5-HYDROXYMETHYLFURFURAL WITH QUATERNARY AMMONIUM SALTS

(71) Applicant: Novamont S.P.A., Novara (IT)

(72) Inventors: Luigi Capuzzi, Novara (IT);
Giuseppina Carotenuto, Novara (IT);
Adriano Ferrari, Novara (IT)

(73) Assignee: Novamont S.P.A., Novara (IT)

( * ) Notice: Subject to any disclaimer, the term of this patent is extended or adjusted under 35 U.S.C. 154(b) by 780 days.

(21) Appl. No.: 17/259,632

(22) PCT Filed: Jul. 12, 2019

(86) PCT No.: PCT/EP2019/068860
§ 371 (c)(1),
(2) Date: Jan. 12, 2021

(87) PCT Pub. No.: WO2020/011996
PCT Pub. Date: Jan. 16, 2020

(65) Prior Publication Data
US 2021/0292290 A1     Sep. 23, 2021

(30) Foreign Application Priority Data

Jul. 13, 2018     (IT) ........................ 102018000007204

(51) Int. Cl.
*C07D 307/46* (2006.01)
*B01D 61/02* (2006.01)
*B01D 61/44* (2006.01)
*B01D 61/58* (2006.01)

(52) U.S. Cl.
CPC ......... *C07D 307/46* (2013.01); *B01D 61/027* (2013.01); *B01D 61/029* (2022.08); *B01D 61/44* (2013.01); *B01D 61/58* (2013.01)

(58) Field of Classification Search
CPC .................................................. C07D 307/46
See application file for complete search history.

(56) References Cited

U.S. PATENT DOCUMENTS

| | | | | |
|---|---|---|---|---|
| 9,611,241 | B2 * | 4/2017 | Boussie | ............... C07D 307/50 |
| 10,030,001 | B2 * | 7/2018 | Bastioli | ............... C07D 307/46 |
| 2004/0099603 | A1 * | 5/2004 | Livingston | ............... B01J 31/26 210/651 |
| 2017/0015642 | A1 | 1/2017 | Sokolovskii et al. | |

FOREIGN PATENT DOCUMENTS

| | | |
|---|---|---|
| CN | 101811066 A | 8/2010 |
| CN | 106029642 A | 10/2016 |
| CN | 107001305 A | 8/2017 |
| EP | 2 371 973 A1 | 10/2011 |
| EP | 2 601 182 B1 | 9/2015 |
| JP | 2017-532339 A | 11/2017 |
| WO | WO 2010/067785 A1 | 5/2012 |
| WO | WO 2014/180979 A1 | 11/2014 |
| WO | WO 2015/113060 A2 | 7/2015 |
| WO | WO 2016/059205 A1 | 4/2016 |
| WO | WO 2016059205 * | 4/2016 ........... C07D 307/46 |
| WO | WO 2017184545 * | 10/2017 ........... C07D 307/46 |

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/ZRegistry (CAS RegistrySM) Sep. 2016 2 pages.*
Yoon, Journal of Membrane Science 261 (2005) 76-86.*
Subbiah, Green Chemistry (2013), 15(10), 2849-2853.*
Cheng, Green Chem., 2018, 20, 997-1006.*
Taraban'ko, Chemistry for Sustainable Development 13 (2005) 551-558.*
Souza. Challenges 2012, 3, 212-232.*
Zhou, Egyptian Journal of Petroleum (2017) 26, 477-487.*
Yu, Bioresource Technology 238 (2017) 716-732.*
PCT/EP2019/068860, Aug. 21, 2019, International Search Report and Written Opinion.
PCT/EP2019/068860, Oct. 28, 2020, International Preliminary Report on Patentability (Chapter II).

(Continued)

*Primary Examiner* — Nizal S Chandrakumar
(74) *Attorney, Agent, or Firm* — Wolf, Greenfield & Sacks, P.C.

(57)     ABSTRACT

The present invention relates to a process for the production and separation of 5-hydroxymethylfurfural (HMF) comprising the steps of: (1) dehydrating at least one saccharide selected from the group consisting of monosaccharides having 6 carbon atoms and disaccharides, oligosaccharides and polysaccharides formed from units having 6 carbon atoms or mixtures thereof, in the presence of water and of at least one quaternary ammonium salt, at a temperature between 80-130° C., obtaining a reaction mixture comprising the quaternary ammonium salt, HMF and any unreacted saccharide; and (2) subjecting the said reaction mixture to at least one membrane separation operation selected in the group consisting of nanofiltration, reverse osmosis, electrodialysis and their combinations, obtaining an aqueous permeate comprising HMF and a retentate comprising quaternary ammonium salt, wherein both the dehydration of step (1) and the separation operations of step (2) are carried out in the absence of organic solvents.

4 Claims, No Drawings

(56)                    References Cited

OTHER PUBLICATIONS

International Search Report and Written Opinion for International App. No. PCT/EP2019/068860 mailed Aug. 21, 2019.

International Preliminary Report on Patentability (Chapter II) for International App. No. PCT/EP2019/068860 dated Oct. 28, 2020.

Alberti et al., Layered and pillared metal(IV) phosphates and phosphonates. Adv Mater. Apr. 1996;8(4):291-303. doi: 10.1002/adma.19960080405.

Brunauer et al., Adsorption of Gases in Multimolecular Layers. J Am Chem Soc. Feb. 1, 1938;60(2):309-19. doi: 10.1021/ja01269a023.

Carniato et al., Ti-POSS covalently immobilized onto mesoporous silica: A model for active sites in heterogeneous catalytic epoxidation. Inorganica Chim Acta. Jan. 15, 2012;380:244-51. doi: 10.1016/j.ica.2011.11.051.

Carniato et al., Titanosilsesquioxane anchored on mesoporous silicas: a novel approach for the preparation of heterogeneous catalysts for selective oxidations. Chemistry. 2008;14(27):8098-101. doi: 10.1002/chem.200801241.

Jadhav et al., Conversion of d-glucose into 5-hydroxymethylfurfural (HMF) using zeolite in [Bmim]C1 or tetrabutylammonium chloride (TBAC)/CrC12. Tetrahedron Lett. Feb. 22, 2012;53(8):983-5. doi: 10.1016/j.tetlet.2011.12.059.

Tegehall, Synthesis of crystalline titanium (IV) phosphates by direct precipitation from Ti (III) solutions and ion exchange properties of some of the prepared phases. Acta Chem Scand. 1986;A40:507-14.

Yuan et al., Catalytic conversion of glucose to 5-hydroxymethyl furfural using inexpensive co-catalysts and solvents. Carbohydr Res. Sep. 27, 2011;346(13):2019-23. doi: 10.1016/j.carres.2011.06.007. Epub Jun. 12, 2011.

[No Author Listed], Membrane Filtration Guidance Manual. United States Environmental Protection Agency. EPA 815-R-06-009. Nov. 2005:332 pages.

* cited by examiner

PROCESS FOR THE PRODUCTION AND SEPARATION OF 5-HYDROXYMETHYLFURFURAL WITH QUATERNARY AMMONIUM SALTS

RELATED APPLICATIONS

This application is a National Stage Filing under 35 U.S.C. § 371 of International Patent Application Serial Number PCT/EP2019/068860, filed Jul. 12, 2019, which claims the benefit of Italian Patent Application Serial Number 102018000007204, filed Jul. 13, 2018, each of which is herein incorporated by reference in its entirety.

The project which led to the invention was financed by the Bio Based Industries Joint Undertaking Public-Private Partnership as part of the European Union Horizon 2020 research and innovation programme under Grant Agreement No. 745766.

The present invention relates to a process for the production and separation of 5-hydroxymethylfurfural (HMF) from saccharides through the use of quaternary ammonium salts.

In particular the present invention relates to an efficient process through which highly pure 5-hydroxymethylfurfural (HMF) can be produced and separated from saccharides in high yields.

HMF is a material of significant importance for obtaining a number of useful intermediates such as for example 2,5-furandicarboxylic acid, 2,5-dimethylfuran and 2,5-(di-hydroxymethyl)furan from renewable sources.

The most direct synthesis route for obtaining HMF is acid-catalysed dehydration of monosaccharides having 6 carbon atoms such as fructose and glucose, or disaccharides and polysaccharides derived from these such as saccharose and inulin, yielding HMF through eliminating 3 water molecules per monosaccharide unit:

$$C_6H_{12}O_6 \rightarrow HMF + 3H_2O$$

The conversion may be performed in solvents of various kinds: water, aprotic dipolar solvents (for example dimethylsulfoxide, N-methyl-2-pyrrolidone, N,N-dimethylformamide, N,N-dimethylacetamide), two-phase systems comprising water and organic solvents (for example 2-butanol, 4-methyl-2-pentanone), ionic liquids (for example N-methyl-2-pyrrolidone methylsulfonate, 1-ethyl-3-methyl-imidazole chloride, 1-butyl-3-methylimidazole chloride, 1-butyl-3-methylimidazole tetrafluoroborate).

Various catalyst systems have been used hitherto to perform the conversion, such as for example acid catalysts of the mineral acids type, acid ion exchange resins, zeolites, supported heteropolyacids, metal chlorides (for example $FeCl_3$, $CrCl_2$, $SnCl_4$).

The acidity of the catalysts can however also favour the rehydration of HMF and subsequent fragmentation to yield levulinic and formic acids, or its oligomerisation or polymerisation to yield further by-products which help to lower the overall reaction yield.

Alkylammonium salts have also recently been suggested as catalysts or solvents for this type of reaction (patent application CN 101811066; "Tetrahedron Letters", 53, 2012, pp. 983-985; "Carbohydrate Research", 346, 2011, pp. 2019-2023), with HMF yields ranging from 45% to 70% depending upon the starting saccharide used.

In every case, although good conversions to HMF can be obtained with combinations of some of these solvents and catalysts, in particular from fructose, because of its high solubility in water, its low melting point (30° C.-34° C.) and the relative thermal instability of HMF, it nevertheless remains difficult to separate it out from the reaction medium and by-products and obtain it as highly pure isolated product. In fact, HMF yields reported in the literature are generally calculated analysing the reaction mixtures (for example by HPLC) and are not determined on the basis of the quantity of product actually isolated and purified.

For example, the use of high boiling point water-soluble solvents such as dimethyl sulfoxide generally requires separation by fractional distillation and subsequent column chromatography. The use of two-phase organic water/solvent systems, ionic liquids or ammonium salts generally requires laborious extractions with substantial quantities of organic solvents to separate out and recover the product.

Again in the process described in Italian patent application no. NO2013A000003, which through combining particular alkylammonium salts with specific catalysts makes it possible to obtain high yields of HMF, complex operations are nevertheless required to recover the HMF, salt and catalyst, and to recycle the solvents used.

Specifically, the methods described hitherto in the literature might be usable on a laboratory scale for preparation of the material in quantities of the order of grams, but are not in fact suitable for the production of large quantities of HMF on an industrial scale, from either the practical point of view or from the point of view of process economics. Again the process described in patent application WO 2016/059205A1, although it allows HMF to be synthesised on an industrial scale, nevertheless requires the use of organic solvents or distillation operations to recover the reaction product.

The applicant has now surprisingly found that by preparing HMF through heating a reaction mixture comprising a saccharide, a quaternary ammonium salt and water not only can high reaction yields be obtained, even in the absence of a catalyst, but the HMF produced can also be easily separated from the reaction mixture through membrane separation operations, such as for example membrane filtration operations. The mild process conditions, both during the saccharide dehydration step and during the HMF separation step make it possible to minimise the conversion of HMF into by-products. At the same time, because the operations of separating out HMF using a membrane are effective even in the absence of organic solvents, subsequent operations for recovery of the salt are consequently considerably simplified.

The resulting process is therefore suitable for the production and separation of highly pure HMF in high yield even on an industrial scale and also, as it does not require the help of organic solvents, it has further advantages from the environmental and process economics points of view in comparison with known processes.

One object of the present invention is therefore a process for the production and separation of 5-hydroxymethylfurfural (HMF) which comprises the steps of:

1) dehydrating at least one saccharide selected from the group comprising or, alternatively, consisting of monosaccharides having 6 carbon atoms and disaccharides, oligosaccharides or polysaccharides formed from 6 carbon atom units or mixtures of these in the presence of water, at least one quaternary ammonium salt and, optionally, an acid catalyst, at a temperature of between 80° C. and 130° C., and preferably keeping it stirred for a time of between 1 minute and 240 minutes, obtaining a reaction mixture including the quaternary ammonium salt, HMF and possibly unreacted saccharide;

2) subjecting said reaction mixture to one or more separation operations using a membrane selected from the group consisting of nanofiltration, reverse osmosis, electrodialysis and their combinations, obtaining an aqueous permeate containing HMF and a retentate comprising quaternary ammonium salt, wherein both the dehydration step 1) and the separation operations of step 2) are carried out in the absence of organic solvents.

The retentate obtained in step 2), comprising the quaternary ammonium salt, any possibly unreacted saccharide and the optional acid catalyst, may be advantageously reused in step 1) of the process as such, or after first being washed and/or receiving various purification treatments, adding suitable quantities of fresh saccharide and water.

Through said separation operation performed using membrane separation in step 2) a substantial quantity of salt can effectively be separated in the retentate and in the absence of organic solvents, substantially simplifying subsequent HMF purification operations.

Said separation operations in step 2) are further simplified if fructose is used as the starting saccharide. The latter is in fact substantially wholly converted into HMF during step 1), thus helping to further reduce the formation of dehydration by-products and improve the yield and purity of the HMF in the permeate.

The minimum amounts of quaternary ammonium salt and secondary components render the HMF composition obtained through the process according to the invention particularly suitable for use as starting material for the preparation of oxidised derivatives, such as for example furandicarboxylic acid, with a high degree of purity. The latter oxidised derivatives can in turn advantageously be used for example as monomers in polymerisation reactions.

The present invention therefore also relates to an HMF composition, in which the purity of the said HMF is greater than 98.5% by weight, said composition comprising at least one quaternary ammonium salt in a quantity, converted into nitrogen atoms, of more than 0, preferably more than 0.001%, and less than 0.25%, preferably less than 0.15% and even more preferably less than 0.02% by weight with respect to the weight of HMF.

The purity of the HMF is for example determined by HPLC/UV analysis with external calibration. For example, the HPLC/UV analysis may be performed using a column of the *"Phenomenex Gemini NX-C18"* type (150 mm×3.0 mm×5 µm; flow: 0.5 mL/min; column temperature: 30° C.) with, as eluents, (A) a 1% by volume aqueous solution of HCOOH and (B) acetonitrile, with the following gradient:

| min | % vol. A | % vol. B |
|---|---|---|
| 0 | 95 | 5 |
| 5 | 90 | 10 |
| 10 | 60 | 40 |
| 15 | 10 | 90 |
| 17 | 10 | 90 |
| 20 | 95 | 5 |
| 22 | 95 | 5 |

Nitrogen content is for example determined through elemental analyses or ion chromatography analyses using a conductivity indicator (IC-CD). The quantity of nitrogen deriving from the quaternary ammonium salt may for example be determined stoichiometrically following quantification of the ammonium cation against an external standard performing the IC-CD chromatographic analysis using a column of the Metrosep C4-100 type (100 mm×4.0 mm×5

µm; flow: 1.0 mL/min; column temperature: 30° C.) and, as eluent, a mixture of aqueous nitric acid (7.5 mmol/L) and 20% v/v acetonitrile.

Said HMF composition forming the subject matter of the present invention further optionally comprises one or more components selected from the group comprising: organic acids, compounds having at least one ketone or aldehyde functional group (other than HMF), dimers, oligomers and humins, formed as by-products in the dehydration reaction of the starting saccharides, said components being advantageously present overall in a quantity from for example 0.0001% to 1% or less, and preferably 0.5% or less, and even more preferably 0.2% by weight or less with respect to the weight of HMF.

Examples of such components are levulinic acid, furyl-hydroxymethylketone, acetic acid, formic acid, dihydroxyacetic acid, dihydroxyacetone, hydroxy[5-hydroxymethyl)furan-2-yl]acetic acid, 4-hydroxypent-3-enoic acid, 2-hydroxyacetic acid, 3-methylbutanoic acid, 2-keto-gluconic acid, 5-hydroxy-3-methylhexa-3,5-dienoic acid, 3-methyl-5-keto-3-hexanoic acid, (3z)-4-hydroxypent-3-enoic acid, 3-(2H)-furanone, 2-ketogluconic acid, 3-methylgluconic acid, furfural, difructose dianhydride, 5,5'-(oxymethanediyl)difuran-2-carbaldehydes, fructopyranose, 2,6-anhydro-β,δ-fructofuranose.

The fructose content in the HMF composition according to the invention (which may be present as a residue of the preparation process) is advantageously 3% by weight or less with respect to the weight of HMF, preferably 2% or less and more preferably 1% by weight or less with respect to the weight of HMF. The fructose content may for example be determined by IC-PAD analysis using a column such as Metrosep Carb 2 (250 mm×4.0 mm×5 µm; flow: 0.7 mL/min; column temperature: 30° C.) and isocratic elution of an aqueous solution of NaOH.

According to one particularly advantageous aspect the HMF composition obtained by the process according to the invention contains furfural in quantities of 0.10% by weight or less with respect to the weight of HMF, more preferably 0.05% or less and even more preferably 0.025% or less. Furfural in fact readily oxidises to 2-furancarboxy acid, which is a limiting impurity in the polymerisation process acting as a terminal member of a chain.

A further limiting impurity in the polymerisation process comprises furyl hydroxymethyl ketone, the percentage by weight of which with respect to HMF in the composition obtained by the process according to the present invention is preferably 1% or less, preferably 0.5% or less and even more preferably 0.2% or less.

Obtaining said HMF composition in the form of an aqueous solution makes it particularly advantageous, without the need for preliminary preparatory treatments such as for example the removal of organic solvent, for use in processes for the preparation of furandicarboxylic acid in an aqueous environment and in the presence of oxygen (or gas containing oxygen) and an appropriate catalyst, such as for example the process described in patent EP 2 601 182 B1.

Such HMF oxidation precesses require the presence of metal catalysts (e.g. belonging to the platinum group i.e. platinum, palladium, iridium, rhodium, ruthenium, osmium) which could be inhibited by the presence of significant amounts of nitrogen in the HMF composition. Without being bonded to any theory, it is believed that nitrogen compounds can form complexes with such precious metals, thus inhibiting the catalyst and reducing its selectivity with respect to 2,5-furandicarboxylic acid.

Another object of the present invention is therefore the use of a HMF composition having a purity of the said HMF greater than 98.5% by weight and comprising at least one quaternary ammonium salt in a quantity, converted into nitrogen atoms, of more than 0, preferably more than 0.001%, and less than 0.25%, preferably less than 0.15% and even more preferably less than 0.02% by weight with respect to the weight of HMF, for the preparation of 2,5-furandicarboxylic acid, preferably in an aqueous environment and in the presence of oxygen (or gas containing oxygen) and a metal catalyst.

The process for the synthesis of HMF according to the present invention will now be described in greater detail.

Examples of saccharides which can be used to obtain HMF through dehydration according to the present process are monosaccharides such as fructose, glucose, galactose, mannose, disaccharides such as saccharose, maltose, lactose, cellobiose, oligosaccharides such as oligofructose containing from 3 units to 10 units of fructose and polysaccharides such as fructanes (e.g. inulin), starch, cellulose.

Specific examples of oligofructose are those having the formula GFn, where G represents the glucose unit, F the fructose unit, and n the number of fructose units between 3 and 10.

Preferred polysaccharides are polysaccharides which are soluble in water at process temperatures (i.e. 80° C.-130° C.), such as for example inulin. Oligosaccharides and polysaccharides which are poorly soluble or insoluble in water may however be used, preferably after prior hydrolysis treatment, for example after acid or enzyme hydrolysis.

The saccharides preferably used in the process according to the present invention are selected from the group comprising or, alternatively, consisting of fructose, glucose, saccharose, inulin or mixtures thereof.

One particularly preferred saccharide is fructose. Among the mixtures, mixtures of saccharides which differ from each other, such as those deriving from the hydrolysis of inulin, and in particular mixtures of glucose and fructose, are preferred.

As far as the quaternary ammonium salt according to the present invention is concerned, quaternary ammonium salts of formula $R_3R'N^+X^-$ are preferred, in which:

R, which may be the same or different, represents a substituted or unsubstituted $C_1$-$C_{16}$ alkyl group;

R' belongs to the group comprising: hydrogen, substituted or unsubstituted $C_1$-$C_{16}$ alkyl group, substituted or unsubstituted monocyclic aryl group;

$X^-$ represents an anion selected from chloride, bromide, iodide, fluoride, hydroxide, $BF4^-$, $PF_6^-$.

The R group is preferably selected from $C_1$-$C_4$ alkyl groups, which may be the same or different; methyl, ethyl, propyl, isopropyl, butyl and isobutyl groups are preferred.

R' is preferably selected from hydrogen (H) and linear or branched substituted or unsubstituted $C_1$-$C_{16}$ alkyl groups; methyl, ethyl, propyl, isopropyl, butyl, isobutyl, sec-butyl, t-butyl, benzyl, phenyl, hexyl, octyl, dodecyl and pentadecyl groups being preferred.

Possible substituents of the R and R' alkyl groups are preferably selected from halogens, carbonic groups, carboxyl groups, hydroxyl groups, ester groups, $R_2R'N^+$ groups.

$X^-$ preferably represents a halide or a hydroxide anion.

According to one aspect of the invention, quaternary ammonium salts having a molar mass of 220 g/mol or more, preferably 250 g/mol or more and even more preferably 270 g/mol or more, are preferred.

Quaternary ammonium salts conveniently used are selected from the group comprising: tetraalkylammonium salts having fluorinated and non-fluorinated chains, ammonium salts having asymmetrical aliphatic and non-aliphatic groups, bis-quaternary ammonium salts, trialkylammonium salts. Of these, tetraalkylammonium salts are particularly preferred.

Tetraalkylammonium salts which may conveniently be used in the process according to the present invention are tetraalkylammonium halides or hydroxides, preferably having $C_1$-$C_{15}$, more preferably $C_1$-$C_4$, alkyl groups, optionally substituted with hydroxyl groups. The preferred tetraalkylammonium salts are chlorides and bromides, such as for example tetramethylammonium chloride, (2-hydroxyethyl) trimethyl-ammonium chloride (choline chloride), tetraethylammonium chloride, tetrapropylammonium chloride, tetrabutylammonium chloride, tetramethylammonium bromide, tetraethylammonium bromide, tetrapropylammonium bromide and tetrabutylammonium bromide. Bromides are particularly preferred.

Tetrapropylammonium chloride, tetrabutylammonium chloride, tetrapropylammonium bromide and tetrabutylammonium bromide are particularly preferred.

According to one aspect of the invention, the preferred tetraalkylammonium salt is tetrabutylammonium bromide.

The ratios by weight between the saccharide and the quaternary ammonium salt for use in the process according to the present invention preferably range from 1:10 to 3:1, more preferably from 1:6 to 2:1, even more preferably from 1:5 to 1:1. Advantageously the ratio by weight between quaternary ammonium salt and saccharide at the start of step 1) is 5:1 or less.

Saccharides and quaternary ammonium salts may be fed to dehydration step 1) in any order and at the same or different temperatures, optionally in the presence of water and/or a catalyst. For example, the saccharide and the quaternary ammonium salt may be placed in contact with each other and premixed to give a premix before being fed to the dehydration step.

According to one aspect of the process according to the present invention, said premixing, which gives rise to a premix, is performed at temperatures below the dehydration temperature, preferably at a temperature within the range from ambient temperature (20° C. and pressure of 1 atmosphere) to 90° C., more preferably from 60° C. to 90° C., even more preferably from 70° C. to 90° C. and even more preferably from 80° C. to 90° C., until a homogeneous mixture is obtained.

According to another aspect, said premixing which gives rise to a premix is performed after the saccharide and/or the ammonium salt has been raised to a temperature equal to the reaction temperature or higher, preferably in the range from 80° C. to 100° C. Advantageously the premixing is carried out after the salt has been raised to a temperature of 90° C. or more. In this case it is preferable to heat the ammonium salt to temperatures in the range from 90° C. to 100° C., advantageously in the presence of a quantity of water from 1% to 50%, preferably from 1.5% to 40%, more preferably from 2% to 30%, even more preferably from 2% to 20% by weight with respect to the salt used, and subsequently adding the saccharide (optionally premixed with a sufficient quantity of water to keep it in solution).

As an alternative, the quaternary ammonium salt and the saccharide may be fed to the dehydration step separately. In this case each is advantageously fed at a temperature equal to the reaction temperature; alternatively one of the two (preferably the salt) is preheated to a temperature higher than the reaction temperature, while the other is added at a lower temperature.

In both the case where the quaternary ammonium salt and the saccharide are fed to the dehydration step separately, and that in which the quaternary ammonium salt and the saccharide are previously premixed together, according to a preferred aspect of the present invention at least one of the saccharide and the salt is premixed with water before being fed to the dehydration step.

The water content of the reaction mixture during the dehydration step must be such as to enable the system to remain in the fluid state, but not such as to encourage HMF rehydration phenomena, with consequent degradation to levulinic and formic acids.

Those skilled in the art will readily be able to determine the quantity of water necessary on the basis of the saccharide and the salt used. For example, according to one preferred aspect of the invention in which fructose and tetrabutylammonium bromide (TBAB) are used, at the start of step 1) water is present in a quantity of 10% or less by weight with respect to the sum of the quaternary ammonium salt and said fructose.

This quantity of water is advantageously added to the salt and/or the saccharide before they may be heated.

Step 1) of the process according to the present invention is advantageously preceded by a preliminary step of preheating at least one of the quaternary ammonium salt and the saccharide before the dehydration step, said dehydration being preferably carried out at a temperature of between 90° C. and 120° C.

According to this application, step 1) is referred to as the "dehydration step" and step 2) as the "separation step".

The dehydration step is carried out in the absence of added organic solvents, such as the separation step, so that advantageously the entire process of preparing and isolating HMF does not require the presence of organic solvents.

According to the present invention, the expression "absence of organic solvents" means that an amount of organic solvent less than or equal to 5% by weight, preferably less than or equal to 1% by weight and more preferably less than or equal to 0.1%, with respect to the weight of HMF may be present.

Notwithstanding the high melting points of the quaternary ammonium salts and the saccharide, under the operating conditions of the present process the reaction mixture is not solid, but is in fluid form because of the formation of a eutectic point at around 70° C.-90° C.

This also facilitates transfer of the mixture from one possible preheating area and feeding it to the dehydration step. In the case where the process is carried out continuously, the saccharide and the salt are in fact advantageously premixed and preheated in a reactor separate from that in which the dehydration step is performed; the preheated fluid mixture can then conveniently be fed to the reactor or reactors in step 1) using a common pumping system.

In the case where the process is performed in batch mode, said preheating and the dehydration step are advantageously carried out in the same reactor.

During dehydration step 1) the reaction mixture is kept stirred at a temperature preferably within the range from 80° C. to 120° C. for a reaction time of typically between 1 minute and 240 minutes. The dehydration step is also preferably performed in an inert environment, for example under nitrogen.

Advantageously the dehydration step is performed at a temperature between 85° C. and 110° C., so as to shorten reaction times and avoid the formation of decomposition products associated with high temperatures. Operating in the absence of added catalysts, the temperature is instead held at a value between 95° C. and 120° C., more advantageously from 100° C. to 120° C.

The times for the dehydration step vary on the basis of the manner of operation. In the case in which the dehydration step is performed in batch mode the reaction time is more preferably between 10 minutes and 120 minutes. In the case where it is performed continuously, the retention time in the dehydration reactor or reactors is preferably from 1 minute to 120 minutes and more preferably from 2 minutes to 90 minutes.

The operation is advantageously performed at atmospheric pressure (1 bar) or slightly higher pressures, preferably up to 5 bar, for example 2 or 3 bar. According to another embodiment the pressure may also be held at values below 1 bar (0.1 MPa), for example between 400 and 900 millibars (0.04-0.09 MPa), removing some of the water from the reaction environment.

According to a preferred embodiment, the process according to the present invention comprises a step of premixing the saccharide and water at a temperature of between 40° C. and 70° C., more preferably at a temperature between 55° C. and 65° C., before dehydration step 1). This premixing operation, taking advantage of the increased solubility of the saccharides at such temperatures, allows the starting materials to be fed continuously to the dehydration step and reduce the quantity of water used. According to said continuous embodiment, premixing of poorly soluble or insoluble polysaccharides with water is advantageously preceded by a preliminary hydrolysis operation, for example with acids or enzymes.

Operating at higher temperatures (e.g. from 105° C. to 110° C.) good conversion of the saccharide to HMF, for example higher than 90%, can be achieved even in the absence of catalyst. Operating in the presence of a suitable acid catalyst, reaction temperatures and times are substantially reduced, further limiting the possibility of degradation of HMF.

Said catalyst may be fed during the dehydration step or premixed with the quaternary ammonium salt and/or saccharide before the dehydration step. Preferably it is premixed with water before being fed to the dehydration step.

Acid catalysts which in principle may be used in the process according to the present invention include Bronsted acids and Lewis acids. Mineral acids (for example hydrochloric acid, sulfuric acid, nitric acid, phosphoric acid), organic acids (for example oxalic acid, levulinic acid, maleic acid, p-toluene sulfonic acid, methane sulfonic acid), acid ion exchange resins (for example of the Amberlyst®, Lewatit®, Diaion® type), zeolites, (for example modified with $TiO_2$), heteropolyacids (for example phosphotungstic acid) which may be supported on silica or alumina, metal oxides (for example titanium (IV) dioxide, zirconium oxide) which may be supported on silica or alumina, metal halides (for example zinc chloride, aluminium trichloride, ferric chloride, chromium chlorides, boron trifluoride), metal phosphates (for example zirconium phosphate, titanium phosphate), and doped zirconium hydroxides (for example sulfates and tungstates) may be used.

In the case where homogeneous catalysts, such as for example the mineral or organic acids listed above, are used, said catalysts typically remain in the aqueous permeate, from which they can be recovered by separation and purification treatments using known techniques.

If catalysts of the heterogeneous type are used, that is to say those not soluble in the reaction environment, said catalysts typically remain in the retentate and can be recovered and fed back again to the dehydration step after possible purification and/or reactivation treatments.

Acid catalysts which are particularly preferred for maximising yields of the dehydration reaction are selected from the group comprising: mineral acids, zirconium phosphate $Zr(HPO_4)_2$, titanium phosphate $Ti(HPO_4)_2$, titanium (IV) dioxide $TiO_2$ supported on silica, and phosphotungstic acid $H_3[P(W_3O_{10})_4]$ supported on silica. Of the mineral acids, nitric acid and sulfuric acid are particularly preferred.

According to one aspect of the present invention the dehydration step in the process is performed in the presence of at least one acid catalyst selected from the group comprising:

i) titanium (IV) dioxide, $TiO_2$, supported on silica having a specific surface area from 150 $m^2/g$ to 900 $m^2/g$, calcined at a temperature of between 150° C. and 900° C.;

ii) phosphotungstic acid, $H_3[P(W_3O_{10})_4]$, supported on silica having a specific surface area between 150 $m^2/g$ and 900 $m^2/g$, calcined at a temperature between 150° C. and 900° C.;

iii) zirconium phosphate, $Zr(HPO_4)_2$;

iv) titanium phosphate, $Ti(HPO_4)_2$.

Type i) catalysts may be prepared from silica having the desired specific surface area and a solution of titanium isopropoxide in organic solvent (for example dioxan), separating out the catalyst by filtration and calcining it at the desired temperature, as described for example in Inorganica Chimica Acta, 2012, 380, pp. 244-251.

Type ii) catalysts may be prepared by impregnating silica having the desired specific surface area with a solution of phosphotungstic acid in water, then removing the water at a temperature within the range from 80° C. to 200° C. and calcining at the desired temperature.

The specific surface area of catalyst i) and ii), suitable for use in the process according to the present invention, is preferably between 100 $m^2/g$ and 350 $m^2/g$.

Specific surface area may be measured according to the BET method described in S. Brunauer, P. H. Emmett and E. Teller, J. Am. Chem. Soc., 1938, 60, 309, measuring the quantity of gas adsorbed on the surface of the material.

The specific surface area of mesoporous materials (values from 50 $m^2/g$ to 400 $m^2/g$) is determined by measuring the quantity of nitrogen adsorbed at 77 K and P/Po of approximately 0.3 and assuming a transverse cross-sectional area for nitrogen of 16.2 $Å^2$, after degassing the catalyst sample at 100° C. overnight in vacuum at $10^{-6}$ Torr (approximately 0.13 MPa).

The specific surface area of microporous materials (values from 400 $m^2/g$ to 1000 $m^2/g$) is measured by determining the quantity of helium adsorbed at 4.2 K and P/Po of approximately 0.3 and assuming a transverse cross-sectional area for helium of 1 $Å^2$, after degassing of the catalyst sample at 100° C. overnight under vacuum at $10^{-6}$ Torr (approximately 0.13 MPa).

Catalyst iii) may be prepared as for example described in *Chemistry—A European Journal,* 2008, vol. 14, pp. 8098.

Catalyst iv) may be prepared as for example reported in *Advanced Materials,* 1996, 8, pp. 291-303, or in *Acta Chem. Scand.,* 1986, A40, pp. 507-514.

The quantity of acid catalyst used is preferably between 0.1% and 20% by weight with respect to the saccharide, preferably from 0.2% to 10%, preferably from 0.5% to 2%.

In the case of supported catalysts (i-ii), the quantity of active phase (understood as the chemical species on the inert support capable of promoting the catalytic activity) is preferably between 0.4% and 10% by weight with respect to the saccharide. In the case of phosphotungstic acid $H_3[P(W_3O_{10})_4]$ supported on silica the quantity of active phase is advantageously between 0.5% and 2% by weight with respect to the saccharide.

The dehydration step reaction is preferably performed in one or more vessels fitted with suitable stirring and heating means, suitable for bringing about effective mixing and capable of providing sufficient surfaces for heat exchange.

The dehydration step may be performed in one or more reactors, which are the same or different, and may be located in series.

According to one aspect of the present invention, in the course of the step 1) reaction fresh saccharide, possibly mixed with water, is fed gradually so as to maintain the saccharide/ammonium salt ratio in the reactor constant, monitoring the viscosity of the system as the reaction progresses.

According to one aspect of the invention, it may be advantageous to remove some of said quaternary ammonium salt at the end of dehydration step 1) and before the separation operations by membrane in step 2). This optional removal may be performed for example by one or more centrifuging or settling operations and through this allow not only some of the salt, which can be recycled to step 1) as such or after prior purification operations, to be promptly recovered but it can also facilitate subsequent separation operations. Said removal operation is particularly advantageous in the case where low molecular weight tetraalkylammonium salts, for example of 250 g/mol or less or preferably 220 g/mol or less (e.g. tetraethylammonium bromide) are used.

According to one aspect of the invention, at the desired saccharide conversion level the dehydration reaction of step 1) is quenched by lowering the temperature of the reaction mixture below the reaction temperature, i.e. below 80° C., preferably below 60° C., more preferably below 40° C. and even more preferably at ambient temperature (20-25° C.) or below, in order to minimize side reactions.

According to one advantageous embodiment, at the end of dehydration step 1) and before separation step 2) the process comprises a step of diluting the reaction mixture comprising the quaternary ammonium salt, HMF and possibly unreacted saccharide deriving from step 1) with water (dilution step). The quantity of water added varies depending upon the quantity and nature of the reaction by-products present. Dilution is conveniently performed so as to achieve a ratio between the dry weight of the reaction mixture obtained at the end of step 1) and water that is preferably from 1:2.5 to 1:30 by weight, more preferably from 1:3 to 1:15 by weight and even more preferably from 1:5 to 1:10. Such a water content in the dehydration product facilitates separation of the HMF from the quaternary ammonium salt during the subsequent separation step of the process.

According to a preferred aspect of the invention, the dilution step comprises the addition of two or more aliquots of water, in equal or different amounts and at the same or different temperatures, to the reaction mixture.

In step 2) of the process according to the present invention the optionally diluted reaction mixture undergoes one or more membrane separation operations to separate HMF from the quaternary ammonium salt. Said separation operations, which may be the same or different, are selected from the group comprising nanofiltration, reverse osmosis and electrodialysis; nanofiltration and electrodialysis are preferred.

Step 2) may advantageously comprise two or more membrane separation operations from those listed above, performed in series or in parallel.

According to a preferred aspect of the invention, before or after any dilution and in any event before separation step 2), the process according to this invention comprises an optional step of preliminary purification of the dehydration product to remove compounds of high molecular weight such as humin and oligomers, produced during the dehydration step, for example following HMF degradation reactions. This preliminary purification has the advantage of avoiding problems of excessive fouling of the membrane during step 2).

Said preliminary purification may be performed in accordance with known techniques, for example by means of one or more operations selected from the group comprising settling, centrifuging, microfiltration or ultrafiltration. Advantageously said purification is performed by ultrafiltration, preferably using ceramic membranes.

According to one preferred embodiment of the invention said step 2) comprises one or more nanofiltration operations performed using at least one nanofiltration membrane. Said nanofiltration operation is advantageously preceded by an ultrafiltration operation with the purpose of removing compounds having a higher molecular weight than HMF, such as for example its oligomers and/or humin.

According to another preferred embodiment of the invention, said step 2) comprises one or more electrodialysis (ED) operations.

The ED operation is performed using ion-selective membranes, which separate the salt (anions and cations) from the electrically neutral HMF.

HMF is therefore recovered in the feed stream while the salt ions are recovered in a brine stream; the latter can advantageously be treated and reused in the dehydration step. More advantageously, the brine stream containing quaternary ammonium salt is concentrated to the desired value, for example by evaporation, prior to be reused in the dehydration step.

According to a specific aspect, the ED is advantageously performed with conventional electrodialysis arrangement, preferably using monopolar membranes. The feed stream after ED contains almost completely deionized HMF; the cations and anions, recovered in a single common stream, are conveyed to the brine compartment.

Said ED operation is advantageously preceded by one or more filtration operations, preferably selected from microfiltration, ultrafiltration and nanofiltration, e.g. an ultrafiltration operation, preferably a ceramic ultrafiltration, with the purpose of removing compounds having a higher molecular weight than HMF, such as for example its oligomers and/or humin.

Depending upon the characteristics of the mixture undergoing the separation operations in step 2) of the process, those skilled in the art will be able to select the type of membrane which has to be used, bearing in mind the material of which it is made, its electrochemical properties and its porosity. On the basis of the properties of the material selected those skilled in the art will also be able to readily select optimum operating pH and pressure conditions during each separation operation and to evaluate the desirability of performing one or more diafiltration passes (i.e. dilution of the retentate through the addition of water and repetition of the separation operation).

For example, the separation in step 2) may be effectively performed using either organic membranes of natural origin (e.g. rubbers, polysaccharides) or synthetic origin (e.g. polymer membranes), or inorganic membranes such as for example ceramic, metal or glass membranes.

Of the organic membranes, polyamides, polyimides, polyalkylenes, polyether imides, polyarene ethers, poly(ether ketones), polycarbonates, cellulose acetates and derivatives are preferred.

Specific examples of suitable organic membranes are polysulfones, aromatic polyamides, polypiperazine amide, polyethylene, polytetrafluoroethylene (PTFE), polypropylene, polyvinyl alcohol, polystyrene, polybenzimidazoles (PBI), polyphenylenes, polyphosphazenes, polyvinylidene fluoride (PVDF), polyethersulfones (PES), polyacrylonitrile (PAN), polyvinylchloride (PVC).

Both isotropic (or symmetrical) and anisotropic (or asymmetrical) and composite membranes are suitable. Anisotropic membranes are preferably used.

Porous membranes (i.e. having a pore size between 1 nm and 10 μm, e.g. macroporous >50 nm, mesoporous from 2 nm to 50 nm, microporous from 1 nm to 2 nm) are preferably used in the present process. Dense membranes (having pore sizes <1 nm) may also advantageously be used, in particular after at least one preliminary membrane separation operation. Macro- or meso-porous membranes are preferably used in the preliminary purification step, while the operations for separating a permeate comprising HMF from a retentate mainly comprising quaternary ammonium salt (step 2) are preferably performed using microporous or dense membranes.

Said membranes used in step 2) advantageously have a mean pore size of 5 nm or less, even more advantageously a mean pore size from 2 nm (corresponding to a molecular cut or MWCO of approximately 1000-1200 Da) to 0.7 nm (corresponding to approximately 120-150 Da) in the case of nanofiltration operations, or 1 nm or less (corresponding to approximately 150-200 Da) in the case of reverse osmosis operations.

The membranes may be shaped in different configurations, for example in flat, tubular, capillary or hollow fibre shapes. Flat membranes may be used as such in filter-press type systems, in rotary systems or wound into spiral modules to increase the surface area/occupied volume ratio.

Membrane separation operations according to the invention may be carried out in batch or continuous mode; depending upon circumstances, a filtration method having a normal (perpendicular) or tangential flow regimen respectively is preferably used. Separation operations across a membrane with a tangential flow regimen are preferred.

Nanofiltration operations are preferably performed according to the invention using membranes of materials selected from the group of: polysulfones, polypiperazine amides, polyamides, polyimides.

Electrodialysis is advantageously performed according to the invention, for example by means of monopolar or bipolar technology, using ionic membranes. The ionic membranes may be either cross-linked or porous, and based on materials preferably selected from polystyrenes, polysulfones, polyether imides, polyarene ethers, polyether sulfones, polyether ketones, polyimides, PBI, polyphosphazenes, PVDF, suitably substituted with functional groups.

Based on the technology applied, various arrangements are possible, e.g. bipolar ED can operate with a two or three compartments configuration and different types and numbers of membranes.

Reverse osmosis is advantageously performed according to the invention using membranes based, for example, on aromatic polyamides or polypiperazine amides.

Examples of membranes typically used for ultrafiltration operations which are useful in the purification operations preliminary to step 2) in the present process are membranes based on polyethylene, PTFE, polypropylene, PAN, cellulose acetate, PES, PVDF.

During the separation operation or operations in step 2) the mixture is preferably held at a temperature between ambient temperature (20° C. to 25° C.) and 50° C., more preferably from 35° C. to 45° C.

According to a preferred embodiment of the invention the quaternary ammonium salt used in the dehydration step has a molecular mass of 220 g/mol or more, preferably 250 g/mol or more and even more preferably 270 g/mol or more, and separation step 2) comprises at least one nanofiltration operation. In accordance with this aspect tetraalkylammonium salts selected from the group comprising tetrapropylammonium chloride, tetrabutylammonium chloride, tetrapropylammonium bromide and tetrabutylammonium bromide are particularly preferred. The even more preferred tetraalkylammonium salt is tetrabutylammonium bromide (TBAB).

According to another preferred embodiment of the invention, separation step 2) comprises a filtration operation performed using polypiperazinamide membranes or other similar membranes which enable even low molecular weight ammonium salts, for example below 220 g/mol, to be readily separated out. In accordance with this aspect dehydration step 1) preferably uses tetraalkylammonium salts selected from the group comprising tetraethylammonium bromide (TEAB), tetraethylammonium chloride, tetrapropylammonium chloride, tetrabutylammonium chloride, tetrapropylammonium bromide and tetrabutylammonium bromide. Even more preferred tetraalkylammonium salts are tetraethylammonium bromide (TEAB) and tetrabutylammonium bromide (TBAB).

Separation step 2) is intended to be performed in one or more steps. It may be repeated several times, adding fresh water to the retentate and optionally using different membranes to maximise HMF separation.

According to a preferred aspect of the process the membrane separation operations in step 2) are optionally followed by one or more further separation operations, performed for example by means of chromatography.

The process for the synthesis of 5-hydroxymethylfurfural according to the invention may be carried out either in batch runs or in continuous or semi-continuous mode.

The permeate resulting from step 2) predominantly contains HMF and water. It may possibly contain some of the ammonium salt, the catalyst from step 1) and possibly unreacted saccharide.

According to one aspect of the invention, after separation step 2) the process comprises an optional step of concentrating the aqueous permeate containing HMF. Said concentration step may be performed according to known techniques in order to remove the water present. One or more operations selected from reverse osmosis, pervaporation, evaporation, for example thermocompression evaporation or multiple effect evaporation, may advantageously be used for the purpose.

For example, the permeate undergoes evaporation, preferably at reduced pressure, to remove water from the HMF. Temperature and pressure conditions which make it possible to remove water as rapidly as possible, avoiding exposing the HMF to prolonged heating at temperatures very much higher than ambient temperatures are nevertheless preferred.

Preferably said concentration step is carried out subjecting the permeate to at least one reverse osmosis operation.

The retentate resulting from step 2) predominantly contains quaternary ammonium salt and traces of HMF. It may possibly contain the catalyst from step 1).

After possibly being exposed to purification processes to remove any HMF residues, said retentate may be reused together with fresh saccharide, water and the possible addition of another salt in step 1) of the process. For this purpose the water content may be adjusted by those skilled in the art before reuse by means of known techniques, for example by means of dilution or evaporation operations.

According to an even more preferred aspect the retentates obtained from various separation operations are pooled, for example in a mixer; a mixture of new saccharide and water in a quantity between 10% and 250% by weight with respect to the saccharide is added to these and the resulting mixture again undergoes step 1) of the process.

This process is furthermore advantageous and preferable in the case where the process is operating continuously.

The HMF obtained at the end of the process generally has a high degree of purity, for example over 85%, preferably 90% or higher and more preferably 95% or higher, and is acceptable for possible subsequent chemical conversions, such as for example oxidation to 2,5-furandicarboxylic acid. Alternatively it may undergo further purification processes (for example by crystallisation) where a higher degree of purity is required.

The process according to the invention will now be described on the basis of non-limiting examples.

EXAMPLES

Example 1

Step 1)

350 g of water and 11.5 kg of a quaternary ammonium salt (tetrabutylammonium bromide, TBAB) were progressively added to a vessel having a useful volume of 20 l with a thermostatic jacket and fitted with stirring means, raising the mixture to a temperature of 80° C. 5 kg of fructose were then added. The mixture was heated to 95-100° C. with stirring and 50 g of a 5 M aqueous solution of sulfuric acid was added. The mixture was held at atmospheric pressure for a reaction time of approximately 15 minutes.

At the end of the reaction the mixture was diluted in water in a ratio of 1:1 by weight (quenching). The quenching product so obtained was analysed by HPLC-UV using a "*Phenomenex Gemini NX-C18*" 150 mm×3.0 mm×5 μm column (flow: 0.5 mL/min; column temperature: 30° C.) and a 1% by volume aqueous solution of HCOOH (A) and acetonitrile (B) as eluents using the following gradient (Table 1):

TABLE 1

| min | % vol. A | % vol. B |
|-----|----------|----------|
| 0 | 95 | 5 |
| 5 | 90 | 10 |
| 10 | 60 | 40 |
| 15 | 10 | 90 |

TABLE 1-continued

| min | % vol. A | % vol. B |
|---|---|---|
| 17 | 10 | 90 |
| 20 | 95 | 5 |
| 22 | 95 | 5 |

The mixture substantially comprised HMF, TBAB, unreacted fructose, water and sulfuric acid. The HMF yield in the mixture obtained at the end of the reaction, determined by HPLC analysis with external calibration, was 83% by weight in comparison with the theoretical obtainable from the starting fructose.

The quenching product was then further diluted by adding a quantity of water equal to approximately 10 times the weight of the quenching product at ambient temperature.
Step 2)

The resulting mixture (pH: 3.8) underwent a preliminary ultrafiltration step using a ceramic membrane with pores of 20 nm diameter (nominal cut-off 20,000 Da), at an operating temperature of between 25° C. and 45° C. (membrane surface area: 0.36 m$^2$; permeate flow: 400 L/h/m$^2$), with two diafiltration steps following a permeation step.

The permeate was then sent to a step of nanofiltration using polyamide membrane with a nominal cut-off of 150-300 Da (membrane surface area: 2.4 m$^2$) at a temperature of between 25° C. and 45° C., applying a pressure of 30 bar (permeate flow: 60-10 L/h/m$^2$). With two diafiltration steps following a permeation step saline rejection of 99.8% relative to the TBAB was achieved.

Finally, the permeate resulting from the nanofiltration step was sent to an osmotic filtration step to concentrate the HMF solution, using a polypiperazine amide seawater membrane (membrane surface area: 2.8 m$^2$), at an average temperature of 35° C. and a pressure of 30-35 bar (permeate flow: 26-20 L/h/m$^2$). Through two diafiltration steps following a permeation step a solution of approximately 60.10 g/l of HMF was obtained.

HPLC analysis of this solution confirmed a recovery yield of approximately 81.8% of 5-hydroxymethylfurfural with a TBAB concentration of less than 1% by weight.

Example 2

The procedure in Example 1 was replicated performing the nanofiltration step twice. Before nanofiltration the pH of the permeate obtained from the ultrafiltration step was adjusted to a value of approximately 6.5 through the addition of NaOH.

At the end of the osmotic filtration step an HMF composition, which when subjected to HPLC-UV analysis as in previous Example 1) showed to be 99.8% pure and have an overall furfural, hydroxymethylketone and levulinic acid content of 0.06% by weight, was obtained.

Analysis of the composition by IC-CD chromatography yielded a nitrogen content of 0.001% by weight. The nitrogen content was determined stoichiometrically following quantification of the ammonium cation by means of an external standard performing the chromatographic analysis with a Metrosep C4-100 column (100 mm×4.0 mm×5 μm; flow: 1.0 mL/min; column temperature: 30° C.) and, as eluent, a mixture of aqueous nitric acid (7.5 mmol/L) and 20% v/v acetonitrile.

IC-PAD analysis of the same composition performed using a Metrosep Carb 2 column (250 mm×4.0 mm×5 μm; flow: 0.7 mL/min; column temperature: 30° C.) and isocratic elution of a 200 mM aqueous solution of NaOH revealed a residual fructose content of 0.1%.

Example 3 Comparative

A preheating and a dehydration reaction were performed in a stirred autoclave, maintaining the same weight ratios between the reactants and according to the same procedure as described in Example 3 of WO 2016/059205.

In more detail, 693.8 g of Tetraethylammonium bromide, TEAB) were fed to a batch stirred autoclave with a useful volume of 2 L fitted with an oil thermostatic jacket. In the same autoclave 30.3 g of distilled water were added, setting the temperature of the thermostatic bath to 100° C. When the internal mixture temperature raised up to 85° C., 278.2 g of fructose were charged in the autoclave. During preheating, the charging operations have been realized under nitrogen flow.

In dehydration step (Step 1 according to the process of WO 2016/059205), at a temperature of 97° C. a slurry consisting of 13.6 g of heterogeneous catalyst (10% HPW/SiO2) mixed with 25.7 g of water has been charged to the autoclave. The system has been kept at this temperature and pressure for about 5 minutes more.

The vacuum has then been applied until 23 mbar to remove water. The reaction time in the autoclave, from the charging of catalyst to drying, was approximately of 68 minutes. The product consisted of HMF, TEAB, unreacted fructose and a water content of 7.13 $g_{H2O\ residual}/g_{HMF}$ (%) H2O$_{residal}$/HMF percent weight ratio).

As in separation step 2) of Example 3 of WO 2016/059205, products obtained in step 1) have been discharged from the reactor and passed to a second stirred vessel (extractor) having a volume of 5 l, held at a temperature of 70° C., to which approximately 2 l of 2-butanone were charged. After 2 h mixing, the organic phase was collected and filtered under vacuum (100-300 mbar) on a sintered glass filter with porosity of 10-16 μm to separate out the solid phase containing the TEAB and fructose from the organic solvent containing the extracted HMF.

The HMF was then recovered by evaporation of the 2-butanone from the liquid phase. The evaporation was performed at about 65° C. in two steps, the first at 400 mbar and the second at 150 mbar.

A yield of approximately 89% of HMF having a purity of approximately 98% by weight was obtained.

Analysis of the HMF composition by IC-CD chromatography yielded a nitrogen content of 1.05% by weight. The nitrogen content was determined stoichiometrically following quantification of the ammonium cation as described above in Example 1 according to the present invention.

Example 4

Step 1)

In a batch apparatus of 20 L of volume, about 350 gr of water were heated to a temperature of 90° C. When the temperature of water reached 90° C., about 8 kg of tetraethylammonium bromide (TEAB) were added to the apparatus and mixed with water. At a temperature of 85-90° C., 5 Kg of fructose were added to the mixture and the complete dissolution of TEAB has been observed. Finally, 50 g of a catalytic solution of H2SO4 5M was added to the mixture at a pressure of 1.8 bar and an increase of temperature to 100-103° C. was observed.

The reaction time was of 15 minutes starting from the adding of catalyst. The HMF in the product was quantified by using the HPLC method described in the example 1.

At the end of the dehydration reaction the mixture was diluted in water in order to obtain the following composition (pH=2.1): Hydroxymethylfurfural 10% wt and tetraethyl-ammonium bromide (TEAB) 22% wt (i.e. the weight ratio of HMF over TEAB is 1:2).

Step 2)

Electrodialysis was performed on a stack operated in three-compartment mode with 10 cell-pairs consisting of AR103/CR67 membranes. A heavy cation membrane CR64LMR was placed at the anode electrode and a heavy anion membrane AR103QDR was placed next to the cathode.

The stack was fed via 3 pumps from 3 tanks containing separate streams for the electrode rinse:

Stream 1: Starting feed solution;

Stream 2: Brine (starting fluid is RO water);

Stream 3: Electrode rinse, an H2SO4 solution at 15 mS/cm.

The electric current applied was limited to 7.5 amps. 4 L of starting feed solution (i.e. the diluted mixture from step 1, 33% mass dry) was charged in the feed solution compartment (Starting feed conductivity: 29167 µS/cm). The process temperature was kept at 30° C. During the process, the conductivity of brine and of feed solution was monitored.

A decrease in amperage was observed after 50 minutes although conductivity of all solution was still high, possibly indicating membrane fouling.

The stack was operated at an initial voltage of 5V. The test was runned until amperage dropped to 0.5 amps. The test was stopped when the final feed conductivity reached a plateau of 9875 µS/cm. The test duration was of 250 minutes.

With the aim to verify the desalting during the process, intermediate samples at 90 min (±14200 µS/cm) and at 120 min (±12000 µS/cm) were collected. The obtained results are reported in Table 2:

TABLE 2

| RUN 1 | Desalting (%) |
|---|---|
| Starting Feed (stream 1) | — |
| Feed 90 min. | 53.9 |
| Feed 120 min. | 73.0 |
| Feed 250 min. (5-HMF stream) | 79.1 |

The removal of TEA+Br– from the HMF solution has been obtained with a recovery of 79.1% TEAB in final brine stream.

The invention claimed is:

1. A process for production and separation of 5-hydroxymethylfurfural (HMF), the process comprising steps of:
   1) dehydrating a saccharide in the presence of water and a tetraalkylammonium salt, at a temperature between 80-130° C., obtaining a reaction mixture comprising the tetraalkylammonium salt, HMF and any unreacted saccharide;
      wherein step 1) is carried out in the presence of an acid catalyst;
   2) diluting the reaction mixture with water to form a diluted reaction mixture; and
   3) subjecting said diluted reaction mixture to at least one membrane separation operation selected from the group consisting of nanofiltration, reverse osmosis, electrodialysis and their combinations, obtaining an aqueous permeate comprising HMF and a retentate comprising tetraalkylammonium salt and any unreacted saccharide;
      wherein each of the steps of the process is carried out in the absence of an organic solvent,
      wherein said saccharide is fructose, said tetraalkylammonium salt is tetrabutylammonium bromide (TBAB) and said acid catalyst is selected from sulfuric acid and nitric acid,
      wherein said process comprises, before step 3), a preliminary purification step for removal of high molecular weight compounds, wherein in the said preliminary purification step comprises one or more operations selected from: decantation, centrifugation, microfiltration or ultrafiltration, and
      wherein step 3) comprises one or more nanofiltration operations and said membrane separation operation of step 3) uses a nanofiltration membrane, the nanofiltration membrane having a mean pore size in a range of 0.7 nm to 2 nm.

2. The process according to claim 1, wherein the weight ratio between TBAB and fructose at the beginning of step 1) is less than 5:1.

3. The process according to claim 2, wherein at the beginning of step 1), water is present in amounts less than 10% by weight with respect to the sum of TBAB and fructose.

4. The process according to claim 1, wherein the reaction time of step 1) is comprised from 1 minute and 240 minutes.

* * * * *